US00PP18508P2

(12) United States Plant Patent
Irie

(10) Patent No.: US PP18,508 P2
(45) Date of Patent: Feb. 19, 2008

(54) ***HYDRANGEA* PLANT NAMED 'RIE 05'**

(50) Latin Name: *Hydrangea macrophylla*
Varietal Denomination: RIE 05

(76) Inventor: Ryoji Irie, 3-7 Narutaki Honmachi Ukyoku, Kyoto (JP)

( * ) Notice: Subject to any disclaimer, the term of this patent is extended or adjusted under 35 U.S.C. 154(b) by 9 days.

(21) Appl. No.: 11/525,979

(22) Filed: Sep. 22, 2006

(51) Int. Cl.
*A01H 5/00* (2006.01)

(52) U.S. Cl. ..... Plt./250

(58) Field of Classification Search ..... Plt./250
See application file for complete search history.

*Primary Examiner*—Wendy Haas

(57) ABSTRACT

A new cultivar of *Hydrangea* plant named 'RIE 05' that is characterized by broad upright habit, large dark grey-green leaves, flowers that range in color from yellow-green to light and dark pink, and unique inflorescence development. In combination these traits set 'RIE 05' apart from all other existing varieties of *Hydrangea* known to the inventor.

5 Drawing Sheets

Genus: *Hydrangea.* Species: *macrophylla.*
Denomination: 'RIE 05'.

BACKGROUND OF THE INVENTION

The present invention relates to a new and distinct cultivar of *hydrangea* that is grown for use as an indoor floral potted plant and an outdoor ornamental flowering shrub. The new cultivar is known botanically as *Hydrangea macrophylla* and will be referred to hereinafter by the cultivar name 'RIE 05'.

'RIE 05' resulted from a breeding program that was conducted by the inventor at the inventor's nursery in Kyoto, Japan and began in 1990. The purpose of the breeding program was to produce new varieties of floral potted *hydrangeas* the exhibit new and unique flowers and flower color.

Between May 1990 and May 1993 the inventor assembled a collection of unnamed and unreleased hybrids from a sequence of deliberate pollinations involving the following cultivars, all unpatented, and available in commerce in Japan: *Hydrangea macrophylla* 'Otafuku', *Hydrangea macrophylla,* 'Yamaajisai', and *Hydrangea macrophylla* 'Fijinishiritaki'. The inventor did not record which variety was used as male parent and which as female parent. In May 1993, the inventor carried out a deliberate pollination between one unnamed plant from the inventor's collection as female parent and the variety *Hydrangea macrophylla* 'Sumidanohanabi' (unpatented) as male parent.

The pollination described above produced thirty-five individual varieties, which the inventor considered novel and unusual. One of these individual varieties was selected by the inventor in June 1994 and is the subject of the present invention, 'RIE 05'.

'RIE 05' is a deciduous shrub that exhibits large dark grey-green leaves and individual flowers that range in color from yellow-green to light and dark pink. Selection was based on the distinguishing characteristics of flowers, flower color, and inflorescence development. 'RIE 05' most resembles the "mophead" type of *hydrangea*. "Mophead" type *hydrangeas* produce showy sterile flowers along the outside of the inflorescence, and small inner flowers that are fertile flowers. However, 'RIE 05' is different in that there are no fertile flowers in the inflorescence which consists of sterile flowers only. 'RIE 05' is distinguishable from the parent plants by flower color, and unique inflorescence development, which produces an average of 270 sterile flowers per inflorescence. It is also distinguished by the darkening of the flower color with age and in that a single plant might have inflorescences of different ages and therefore several shades of colors are displayed simultaneously.

The inventor considers that 'RIE 05' is distinct from other varieties of *Hydrangea* known to the inventor in the following respects:

First, whereas other varieties of *Hydrangea* in commerce have four petals per floret on a flat, one-dimensional plane, 'RIE 05' has two to three layers of petals per floret, creating a double-flower appearance.

Second, whereas many novel varieties have been found in, or brought from, Japan in recent years, none appear to have the combination of uniqueness of flower form as above combined with greater vigor and faster growing to flowering stage which typifies 'RIE 05'.

Third, the vigor of 'RIE 05' is evident in its strong thick stems which do not require staking to support the heavy blooms. 'RIE 05', although vigorous, exhibits a shorter internode distance than many other commercial forms of *Hydrangea,* allowing 'RIE 05' to be grown commercially with less or even no application of growth regulating chemical.

'RIE 05' was first asexually propagated by the inventor, in the spring of 1995 in a cultivated area of Kyoto, Japan. The method used for asexual propagation was softwood cuttings. The characteristics of the new *Hydrangea* cultivar named 'RIE 05' have been determined stable and are reproduced true to type in successive generations of asexual propagation.

SUMMARY OF THE INVENTION

The following traits have been repeatedly observed and represent the characteristics of the new *Hydrangea* cultivar 'RIE 05'. These traits in combination distinguish 'RIE 05' from all other commercial varieties of *Hydrangea* known to the inventor. 'RIE 05' has not been tested under all possible conditions and phenotypic differences may be observed with variations in environmental, climatic and cultural conditions, without however, any difference in genotype.

1. *Hydrangea* 'RIE 05' is grown for use as both an indoor floral potted plant and an outdoor ornamental flowering shrub.
2. *Hydrangea* 'RIE 05' exhibits individual flowers that range in color from yellow-green to light and dark pink.
3. *Hydrangea* 'RIE 05' exhibits unique inflorescence development that produces an average of 270 sterile flowers and no fertile flowers per inflorescence.
4. *Hydrangea* 'RIE 05' exhibits inflorescences that change color throughout their blooming period and may have blooms of different ages and colors on the plant simultaneously.
5. *Hydrangea* 'RIE 05' exhibits a broad upright habit.
6. *Hydrangea* 'RIE 05' exhibits large dark grey-green leaves.
7. *Hydrangea* 'RIE 05' is 34.5 cm in height and 45 cm in diameter in a 5-liter container.
8. *Hydrangea* 'RIE 05' is a shrub.
9. *Hydrangea* 'RIE 05' is deciduous.
10. *Hydrangea* 'RIE 05' performs best when planted in loam based moisture retentive soil, in partial shade, with regular water.
11. *Hydrangea* 'RIE 05' is asexually propagated by the method of softwood cuttings.
12. *Hydrangea* 'RIE 05' exhibits rigid, strong basal branches.
13. *Hydrangea* 'RIE 05' is hardy to USDA Zone 7.
14. *Hydrangea* 'RIE 05' blooms continuously from early April to September.

BRIEF DESCRIPTION OF THE DRAWINGS

The accompanying color drawings illustrate the overall appearance of the new *Hydrangea* cultivar 'RIE 05' showing the colors as true as it is reasonably possible to obtain in colored reproductions of this type. Colors in the photographs may differ from the color values cited in the detailed botanical description, which accurately describe the actual colors of the new variety of *Hydrangea* named 'RIE 05'.

The drawing labeled as FIG. 1 depicts a view from above of an individual whole plant growing in the border soil in a frost-protected greenhouse in De Kwakel, The Netherlands. The pH of the soil was in the range of 6.0 to 6.4. The plant is approximately one year old. The plant was produced from a cutting which was rooted and grown in a four inch container, planted into the ground, then pinched to encourage basal branching, then allowed to shoot from the base and allowed to flower in its natural season. The drawing also shows the variation in inflorescence color dependent on the age of the flowers.

The drawings labeled as FIG. 2 to FIG. 5 illustrate a one year old plant of 'RIE 05' which has been grown in a 1.5 liter container in a frost-protected greenhouse in De Kwakel, The Netherlands. The plant was produced from a cutting which was rooted and grown in a four inch container, then transplanted into the 1.5 liter container and pinched to encourage basal branching.

Figure 1:
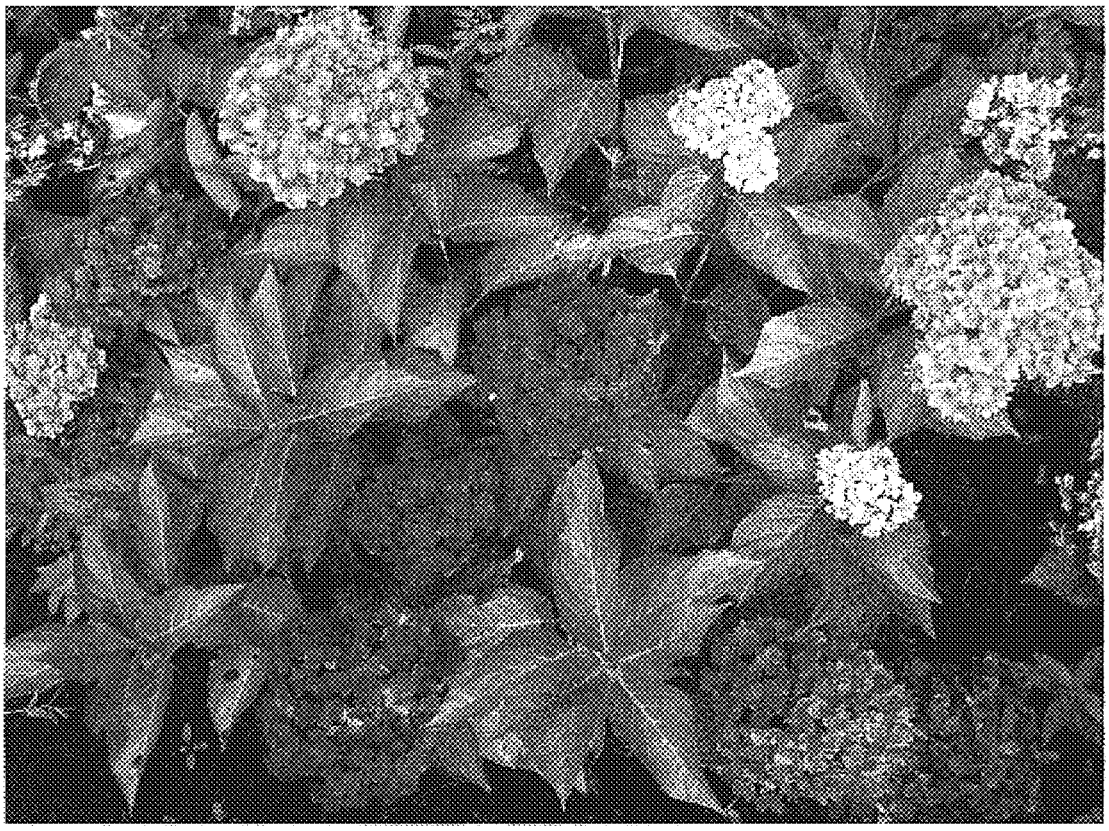
Figure 2:
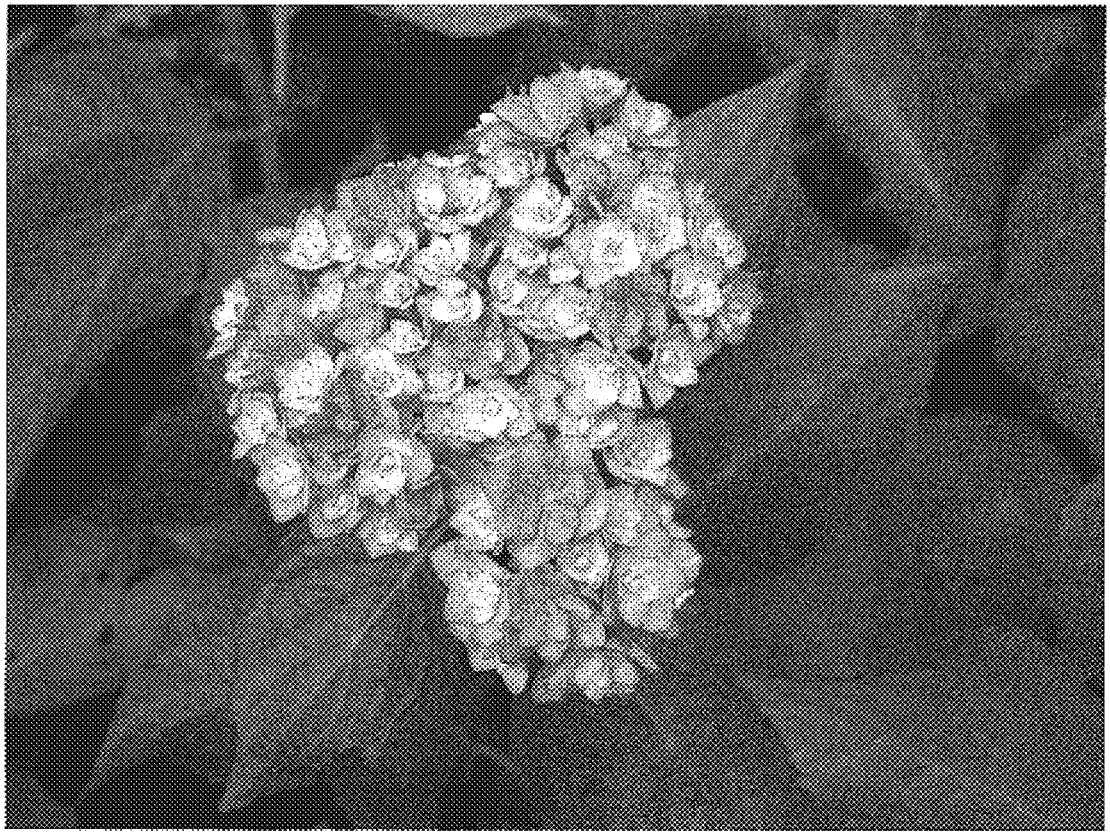
Figure 3:
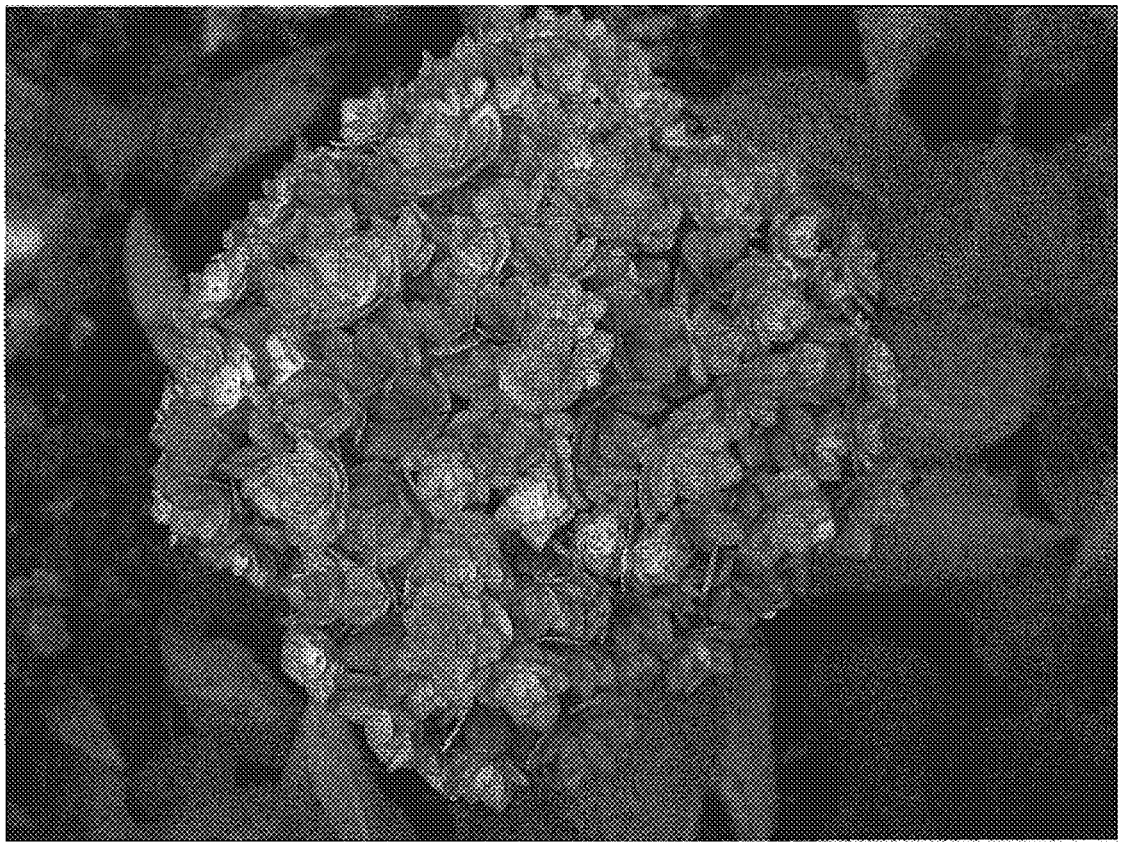

The drawing labeled FIG. 2 depicts the inflorescence of 'RIE 05' at it first developmental stage. The drawing labeled FIG. 3 illustrates the inflorescence of 'RIE 05' at its second developmental stage.

Figure 4:
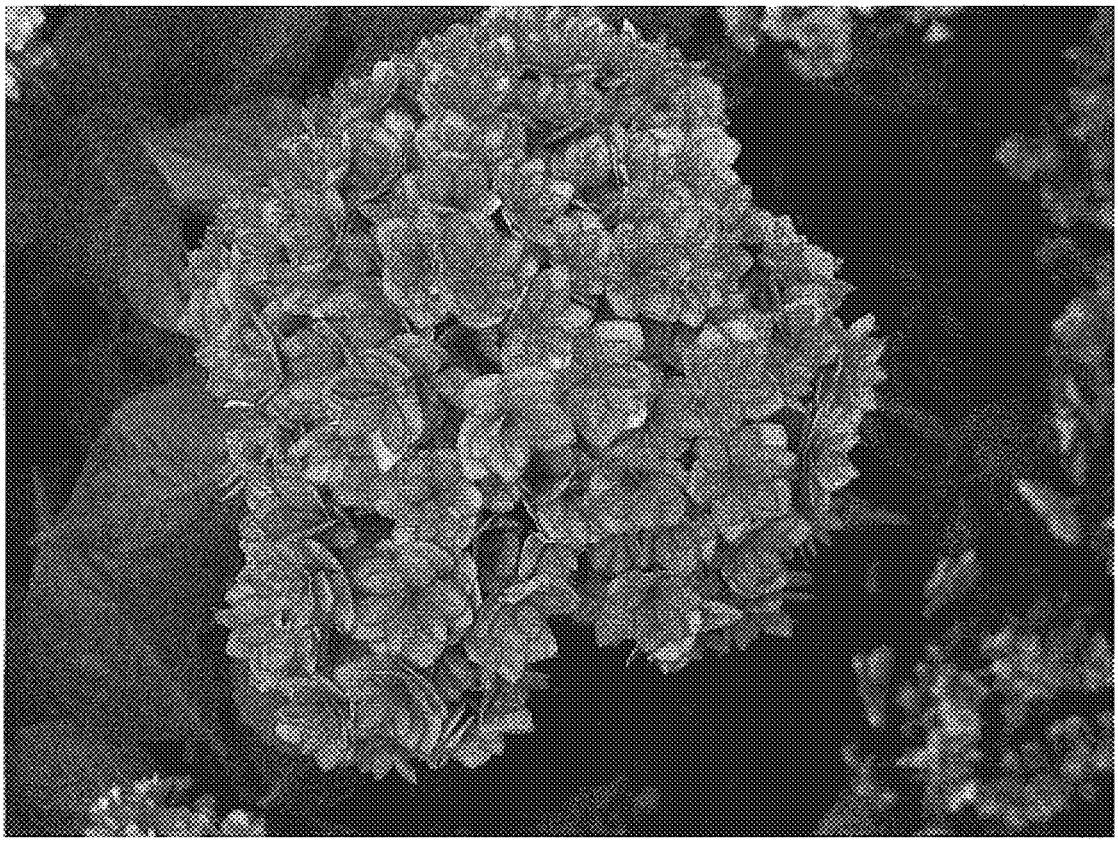

The drawing labeled FIG. 4 shows the inflorescence at its third stage.

Figure 5:
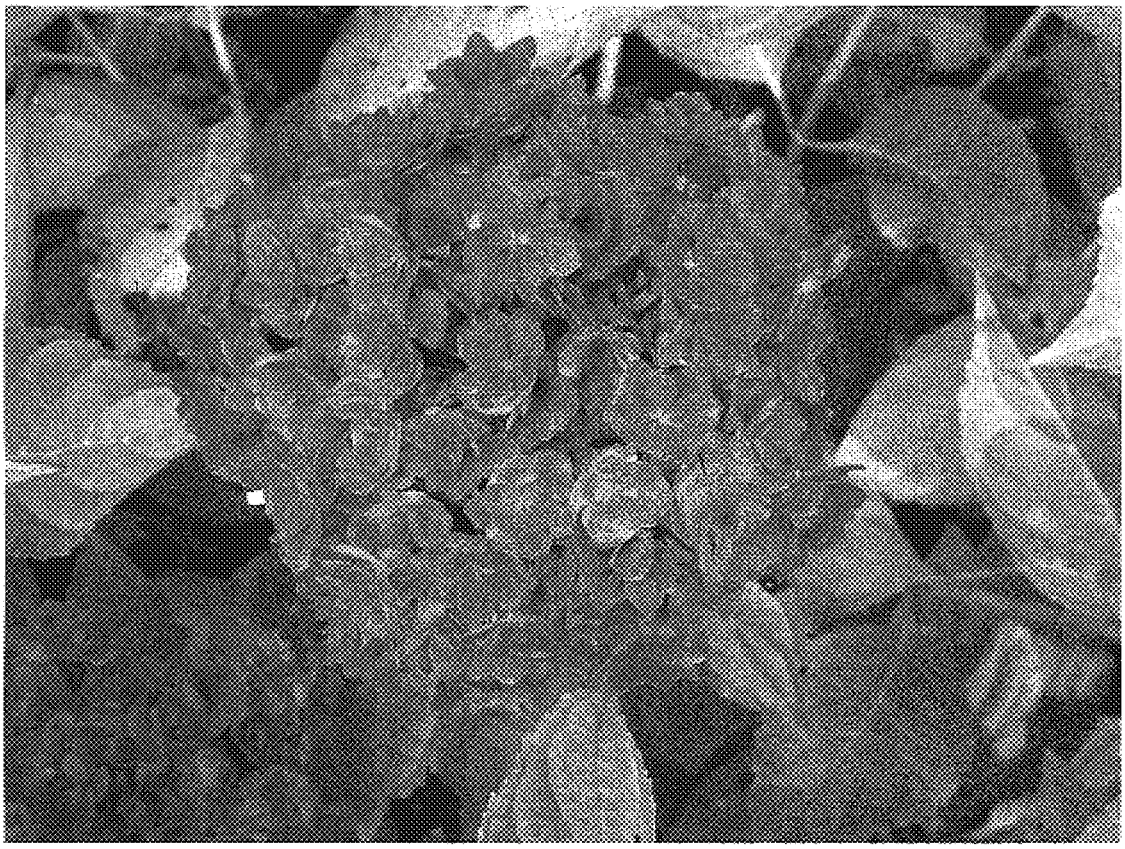

The drawing labeled FIG. 5 shows the inflorescence at its fourth stage.

All drawings were made using conventional techniques and although colors may appear different from actual colors due to light reflectance they are as accurate as possible, by conventional photography.

BOTANICAL DESCRIPTION OF THE PLANT

The following is the detailed description of 'RIE 05' as grown in a greenhouse in De Kwakel, The Netherlands. Data was collected in April 2004 from 1-year-old plants grown in 1.-liter containers. The plants were growing in a peat-based medium and maintained within pH range 6.0–6.4. The color determinations are in accordance with the 2001 Edition of the Colour Chart of The Royal Horticultural Society, London, England, except where general color terms of ordinary dictionary significance are used. The growing requirements are similar to the species.

Botanical classification: *Hydrangea macrophylla* 'RIE 05'.
- *Genus.*—*Hydrangea.*
- *Species.*—*macrophylla.*
- *Denomination.*—'RIE 05'.

Commercial classification: Floral plant, ornamental shrub.

Common name: *Hydrangea.*

Use: Grown for use as a potted indoor plant or as an outdoor ornamental flowering shrub.

Container size: Suggested container size is 1.5 liter.

Cultural requirements: Performs best when planted in loam based moisture retentive soil, in partial shade, with regular water.

Parentage: *Hydrangea macrophylla* 'RIE 05' is a hybrid plant that resulted from the induced cross-pollination of the following parent plants:
- *Female parent.*—An unnamed individual *Hydrangea macrophylla.*
- *Male parent.*—An individual *Hydrangea macrophylla* 'Sumidanohanabi' (unpatented).

Plant description:
- *Blooming seasons.*—Spring and summer (natural season) or year-round if forced.
- *Plant habit.*—Broad upright.
- *Plant type.*—Deciduous shrub.
- *Overall plant shape.*—Broad inverted triangle.
- *Vigor.*—Moderate.
- *Growth rate.*—An average of 15-cm. per month in spring.
- *Plant height.*—34.5 cm in height.
- *Plant diameter.*—45 cm in diameter.
- *Hardiness.*—USDA Zone 7.
- *High temperature tolerance.*—Tolerant to 32° Centigrade.
- *Root system.*—Fibrous.
- *Propagation.*—Propagation is accomplished by the method of softwood cuttings.
- *Time and temperatures to develop roots.*—Approximately 4 weeks is needed to develop roots on an initial cutting, at temperatures of 18° to 20° Centigrade.

*Crop time* (*outdoor plant crop*).—An average of 12 months is needed to produce a commercial container size flowering outdoor plant, from a rooted cutting.

*Temperatures* (*outdoor plant crop*).—From rooted cuttings to commercial size containers, the outdoor crop is grown at natural outdoor temperatures utilizing unheated greenhouses for winter protection.

*Crop time* (*indoor plant crop*).—An average of 4–6 months is needed to produce a commercial container size flowering indoor plant, from a rooted cutting.

*Temperatures* (*indoor plant crop*).—Transplant rooted cuttings to liner pots and keep for a minimum of 6 weeks at below 5° Centigrade to force dormancy. Transplant to 1.5-liter containers and keep at 18° to 25° Centigrade for a minimum or 10 weeks to produce commercial container size flowering plants.

*Disease and pests resistance or susceptibility.*—No susceptibility to pests or disease known to the inventor.

Stem:

*Lateral branches.*—Number: An average of 5 lateral branches. Dimensions: Average length 16.3 cm; average diameter 6 mm. Shape: Rounded. Surface: Slightly glossy. Pubescence: None observed. Strength: Strong. Color: 144A and 144B; at the nodes stems are colored N186C

*Lenticels.*—Present. Quantity: An average of 8 per cm of stem surface. Dimensions: Average length 2 mm; average width 0.5 mm. Color: N186C.

*Branching habit.*—Moderate to sparse basal branching.

*Branching requirements.*—Pinching encourages lateral branching.

*Internode length.*—3.9 cm between nodes.

Foliage:

*Type.*—Deciduous.

*Arrangement.*—Opposite.

*Division.*—Simple.

*Quantity of leaves per lateral stem.*—An average of 10 individual leaves.

*Leaf.*—Shape: Leaves range from broad oval to elliptic-oblong. Dimensions: Average length 10.8 cm; average width 6.8 cm. Apex: Apiculate. Base: Attenuate. Margins: Crenate. Appearance (adaxial and abaxial surfaces): Smooth, slight-glossy surfaces. Pubescence: None present. Venation pattern: Pinnate. Vein color (abaxial and adaxial surfaces): Ranges 144A to 146D. Leaf color (adaxial surfaces): Between 139A and 147A. Leaf color (abaxial surfaces): 137C.

*Attachment.*—Petiolate.

*Petiole.*—Dimensions: Average length 2.0 cm; average diameter 3 mm. Surface: Glabrous. Shape: Cylindrical. Color: 144A.

*Durability of foliage to stress.*—High durability to stress.

*Stipules, tendrils, thorns.*—None observed.

*Fragrance.*—None observed.

Flowers:

*Flower arrangement.*—Terminal inflorescence consisting of sterile flowers only.

*Inflorescence type.*—Compound corymb.

*Inflorescence dimensions.*—Average height 11 cm; average diameter 13.8 cm.

*Quantity of flowers per inflorescence.*—An average of 270 flowers.

*Flowering habit.*—An individual plant blooms continuously from early April to September.

*Bud.*—Dimensions: Average of 6 mm in length: 2 mm in diameter. Shape: Ovate. Apex: Obtuse. Color: 145C.

*Flower aspect.*—Uprights to outward.

*Rate of opening.*—An average of 10% of the flowers on an individual plant open at once, and all the flowers on an individual plant have opened by 6 weeks.

*Flower shape.*—Rotate in shape.

*Persistent or self-cleaning.*—Persistent.

*Peduncle.*—Shape: Cylindrical. Dimensions: Average length 5.1 cm; average diameter 3.5 mm. Color: 144A. Angle: Average angle is 40°. Strength: Strong.

*Lenticels.*—Present on peduncle. Color: 187B. Dimensions: 2 mm in height, 0.3 mm in width.

*Individual flowers.*—Dimensions: Average diameter 2.9 cm; average depth 1.2 cm. Tepal: Dimensions: Average length 1.5 cm; average width 1.2 cm. Appearance: Dull. Surface: Glabrous. Number: An average of 12 tepals per sterile flower. Fused or unfused: Unfused. Shape: Tepals range from rhomboidal to broad elliptic on an individual inflorescence. Margin: Entire. Apex: Rounded to bluntly acute. Color (abaxial surfaces when opening): 149C initially, then 62C and 62D. Color (adaxial surfaces when opening): 149C initially, then 62D with veins 63D. Color (abaxial surfaces when fully opened): Between N66C and 70B. Color (adaxial surfaces when fully opened): 75B with veins 75A. Calyx: None observed. Pedicel: Dimensions: Average length 8 cm; average diameter 1 mm. Angle: Average angle is 35°. Strength: Moderate. Color: 64B. Surface: Glabrous. Pubescence: None observed. Lenticels: None observed.

*Lastingness of flowers.*—An individual flower lasts 4 weeks.

*Flower response time.*—An average of 9 weeks.

*Flower fragrance.*—None observed.

Reproductive organs: None observed.

Seed production: No seed production has been observed to date.

It is claimed:

1. A new and distinct cultivar of *Hydrangea* plant named 'RIE 05' as described and illustrated herein.

* * * * *